United States Patent
Lundh et al.

(10) Patent No.: US 11,116,671 B2
(45) Date of Patent: Sep. 14, 2021

(54) COMPRESSION GARMENT FOR PROVISION OF AN ADJUSTABLE PRESSURE

(71) Applicant: Presscise AB, Herrljunga (SE)

(72) Inventors: Torbjörn Lundh, Billdal (SE); Jonatan Vasilis, Gothenburg (SE); Josefin Damm, Ljung (SE)

(73) Assignee: PRESSCISE AB, Herrljunga (SE)

( * ) Notice: Subject to any disclaimer, the term of this patent is extended or adjusted under 35 U.S.C. 154(b) by 768 days.

(21) Appl. No.: 15/543,354

(22) PCT Filed: Jan. 19, 2015

(86) PCT No.: PCT/EP2015/050775
§ 371 (c)(1),
(2) Date: Jul. 13, 2017

(87) PCT Pub. No.: WO2016/116125
PCT Pub. Date: Jul. 28, 2016

(65) Prior Publication Data
US 2017/0367899 A1    Dec. 28, 2017

(51) Int. Cl.
*A61F 13/08* (2006.01)
*A61F 13/06* (2006.01)
(Continued)

(52) U.S. Cl.
CPC .............. *A61F 13/08* (2013.01); *A61F 13/06* (2013.01); *A61F 13/10* (2013.01); *A61H 1/008* (2013.01);
(Continued)

(58) Field of Classification Search
CPC ........ A61F 13/06; A61F 13/061; A61F 13/08; A61F 13/10; A61F 13/101; A61F 13/104;
(Continued)

(56) References Cited

U.S. PATENT DOCUMENTS 3,570,482 A * 3/1971 Emoto .............. A61F 13/00021
602/76
3,845,769 A   11/1974 Shaw
(Continued)

FOREIGN PATENT DOCUMENTS

WO      WO 01/00118 A1     1/2001
WO      WO 2011/025396 A1  3/2011
(Continued)

OTHER PUBLICATIONS

International Search Report (PCT/ISA/210) dated Sep. 23, 2015, by the European Patent Office as the International Searching Authority for International Application No. PCT/EP2015/050775.
(Continued)

*Primary Examiner* — Keri J Nelson
(74) *Attorney, Agent, or Firm* — Buchanan Ingersoll & Rooney P.C.

(57) ABSTRACT

A compression garment for providing an adjustable pressure towards a body part is disclosed. The compression garment comprises a unitary single sheet of elastic material arranged to encircle the full circumference of a body part, such as a limb or the head. The sheet is folded or arranged to be folded in at least one predefined way, so that the folding forms one or more defined overlap(s) forming at least two overlaying layers of the sheet encircling the full circumference of a part of the body part. Hereby, the pressure profile of the garment can easily be adjusted by making use of the garment in different folded configurations. Markings may further be provided to provide guidance towards the predefined ways of folding.

25 Claims, 12 Drawing Sheets

(51) Int. Cl.
  *A61F 13/10* (2006.01)
  *A61H 1/00* (2006.01)
  *A61F 13/12* (2006.01)
(52) U.S. Cl.
  CPC ............ *A61F 13/061* (2013.01); *A61F 13/101* (2013.01); *A61F 13/104* (2013.01); *A61F 13/107* (2013.01); *A61F 13/12* (2013.01)
(58) Field of Classification Search
  CPC ...... A61F 13/105; A61F 13/107; A61F 13/12; A41B 11/00; A61H 1/008
  USPC ............... 602/22, 60–63, 75; 2/239–242
  See application file for complete search history.

(56) References Cited

U.S. PATENT DOCUMENTS

| | | | |
|---|---|---|---|
| 4,215,687 A | 8/1980 | Shaw | |
| 4,926,851 A * | 5/1990 | Bulley | ............... A61F 13/105 128/856 |
| 6,109,267 A | 8/2000 | Shaw et al. | |
| 6,613,007 B1 * | 9/2003 | Reid, Jr. | ............... A61F 13/08 602/62 |
| 2002/0172781 A1 | 11/2002 | Ricci et al. | |
| 2009/0137938 A1 | 5/2009 | Parivash | |
| 2012/0316480 A1 | 12/2012 | Nolan et al. | |

FOREIGN PATENT DOCUMENTS

| | | |
|---|---|---|
| WO | WO 2014/144790 A1 | 9/2014 |
| WO | WO 2015/007335 A1 | 1/2015 |

OTHER PUBLICATIONS

Written Opinion (PCT/ISA/237) dated Sep. 23, 2015, by the European Patent Office as the International Searching Authority for International Application No. PCT/EP2015/050775.

"Compression Bandage—an overview", ScienceDirect Topics, 2020, obtained from https://www.sciencedirect.com/topics/engineering/compression-bandage accessed on Sep. 28, 2020 (15 pages).

* cited by examiner

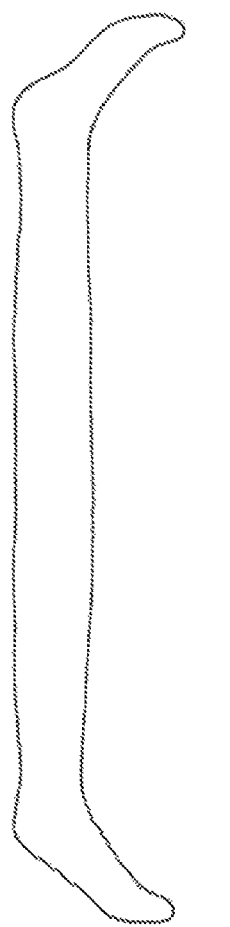
Fig. 10  Fig. 11  Fig. 12
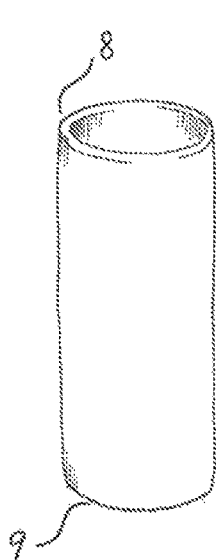
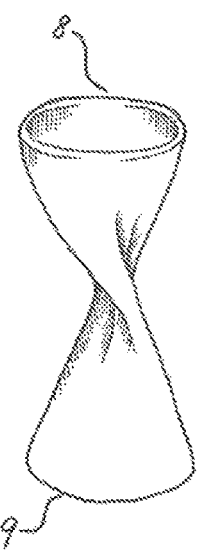
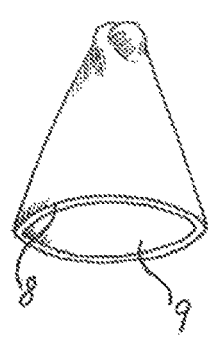
Fig. 13  Fig. 14  Fig. 15  Fig. 16

COMPRESSION GARMENT FOR PROVISION OF AN ADJUSTABLE PRESSURE

TECHNICAL FIELD OF THE INVENTION

The present invention relates to a compression garment providing an adjustable pressure towards a body part, as well as a corresponding method for adjusting the range of compression level applied by a compression garment.

BACKGROUND

Compression garments such as compression socks, tubular bandages, pantyhoses, girdles and sleeves, are being used at several indications such as venous insufficiency, oedema treatment, after surgery or treatment of varicose veins, relief in case of injuries such as subcutaneous bleeding associated with blunt trauma, muscle sprains, to support blood circulation for persons—or animals—that might have poor circulation, have to stand for a long time, to perform (or recover from) sport activities, or other physically demanding activities.

Compression garments are useable to create localized pressure, to inhibit or treat established swelling and to enhance the venous return in individuals with either venous insufficiency or obstruction. For non-medical indications compression garments are applied to reduce the risk of muscle sprain and strains and to improve recovery after physical activities. A particular line of use for compression garments is for compression therapy designed for the purpose of venous oedema. Yet another purpose is to facilitate the transportation of blood in the deep system. In addition, compression is of value to prevent swelling to emerge or reduce risk for venous thrombus formation. Examples of the latter are in connection to surgery or intercontinental flights. Swelling can also commonly be seen in connection to heart failure.

Many medical conditions can be improved by compression therapy. The conditions to be improved include bleeding after surgery or bleeding following trauma. The bleedings following surgery or trauma can be located within different compartments or combination of compartments. These are characterized to be at different levels, depth in relation to the skin surface. Illustrative examples are subcutaneous bleedings following operations for varicose veins, muscular bleeding following orthopedic interventions or blunt trauma in contact sports with bleeding either subcutaneously or in muscles or within both locations in combination. Depending on localization of the bleeding, different pressures need to be applied.

In sports, elastic compression garments are today being used in order to: improve recovery, faster warm up and enhance overall circulation, enhance stability and agility, reduce fatigue and reduce damage.

All indications and problems discussed above are also applicable in different settings in veterinary medicine.

The variety of indications needs a variety of different pressures to be applied for optimal function. Depending on indication (therapy, prevention) and targeted location, the needed pressure to be applied varies. However, providing an appropriate pressure, and especially for compression therapy, is difficult in practice, and there is a great risk that compression is applied in a non-optimal way. Since the needed pressure varies with the indication and condition, the optimal pressure distribution is difficult to reach. For example, if an athlete gets a big contusion, one would like to localize a well-defined pressure profile on the center of that contusion.

Thus, it is a great challenge to be able to provide a desired or given compression distribution in a correct, controllable and repeatable manner.

An ordinary compression garment applies a pressure to a body part for medical purposes, such as to improve the vascular function. The pressure exerted depends primarily on the relative sizes of the body part and compression garment, and to reduce the variation in pressure for body parts of various sizes—that is, to reduce the variation between individuals—the compression garment is usually available in multiple sizes. A common example of such a compression garment is the compression sock, which exerts pressure on a leg.

By varying the circumference of the compression garment in the longitudinal direction, such as giving it a tapered shape, different pressures can be achieved along the body part. For instance, it is often desired to achieve an increase in pressure (a pressure gradient) in the distal direction. Instead of, or as a complement to, varying the circumference one can adjust the elastic properties of the garment along the longitudinal/distal direction.

However, these garments, using the techniques known in the prior art, create a pressure profile that strongly depends on the shape of the body part. For instance, if the body part itself has a strongly tapered shape, the increase in pressure in the longitudinal direction is much less than that for a body part with less tapered shape. A common solution to this problem, as discussed e.g. in U.S. Pat. No. 3,845,769, U.S. Pat. No. 4,215,687 and U.S. Pat. No. 6,109,267, US 2012/0316480, is to construct a garment or boot that uses a set of bands, which may or may not be of high elasticity, that wrap around a body part. By using for instance hook and loop fasteners, it is possible to control the stretching of the bands and thus implicitly also determine the pressure exerted on the body part. If there are multiple bands, it is also possible to vary the pressure along the body part. For instance, it is possible to create a pressure gradient that increases the pressure in the distal direction or to reduce, perhaps only temporarily, the pressure over a sensitive section of the body part.

However, with this approach it is in practice very difficult to achieve a prescribed pressure, even for body parts with essentially circular cross sections. The reason for this is, inter alia, that the exerted pressure depends both on the stretching force in the garment or boot and on the circumference of the essentially circular body part. In the medical literature the relationship between the pressure, the longitudinal force and the circumference is called Laplace's law.

Hence, there is need for a compression garment that will give a predictable and controllable pressure profile for a wide range of body part sizes but at the same time allows the pressure profile to be easily adjusted in a precise manner.

SUMMARY OF THE INVENTION

There is therefore an object of the present invention to provide a compression garment providing an adjustable pressure towards a body part at least partly overcoming the above-discussed deficiencies and drawbacks of the prior art, as well as a corresponding method for adjusting the range of compression level applied by a compression garment.

This object is achieved by means of a compression garment and a method for adjusting the range of compression level applied by a compression garment according to the enclosed claims.

According to a first aspect of the invention there is provided a compression garment providing an adjustable pressure towards a body part, comprising a unitary single sheet of elastic material arranged to encircle the full circumference of a body part, the sheet being folded or arranged to be folded in at least one predefined way, the folding forming one or more defined overlap(s) forming at least two overlaying layers of the sheet encircling the full circumference of a part of said body part.

By "unitary single sheet" is in the context of this application meant a sheet which is formed in one continuous piece. However, this sheet may be arranged in various shapes, such as in a planar disc/plate shape, a torus/doughnut shape, a cylindrical shape, a spherical shape, etc. The sheet is preferably provided as a one-layer material, but may also comprise two or more layers being arranged in a sandwich construction.

By folding in a "predefined way" is in the context of the present invention meant a folding where the shape of the garment, the shape of the enclosed body part, markings or other types of indicia exist which provide clear guidance to the user how to provide the folding to obtain a desired pressure profile.

It has surprisingly been found by the present inventors that by providing the compression garment as a single sheet material, and providing predefined folding possibilities, a compression garment is provided in which various pressure profiles are easily obtained. Further, use of the compression garment to obtain the various pressure profiles can also be made very intuitive, making provision of the desired profile simple, reliable and controllable. Further, this compression garment can be produced very cost-efficiently. Further, the compression garment can easily be provided with a multitude of various folding possibilities, thereby providing a plurality of easily obtainable pressure profiles.

By folding the compression garment, a well-defined increased pressure is obtained in the overlap area, thereby providing adjustability of the pressure exerted by the compression garment. In the simplest case, this adjustability may be provided in only two states: folded and unfolded. However, two or more predefined folding possibilities may be provided, providing additional pressure profiles. The folding may be a single folding, providing a doubling of the material in an overlap area. However, the folding may also be a double fold, providing three layers of material in the overlap area, and even more complex foldings may be used.

The compression garment may be of a general type, applicable to two or more different body parts, such as the upper or lower part of a leg, the upper and lower part of an arm, etc. However, the compression garment may also be dedicated to a specific body part, such as the head. Specifically, the compression garment may be a head covering, a leg covering, to extend from the knee to the ankle, a stocking to extend between the foot and a part or all of the leg, a sock, being a short stocking, a pantyhose, extending beyond the legs, a tubular bandage, a sleeve to cover all or a part of the arm, or a girdle to cover the lower torso, etc.

The compression garment may be useable on various body parts, such as on a body limb, such as an arm, or leg, and a body head.

The sheet preferably comprises at least one marking, indicating a defined overlap for a part of the sheet folded over another part of the sheet. The at least one marking may e.g. preferably indicate a plurality of various overlaps, providing a corresponding plurality of compression profiles. By the provision of such markings, a desired degree of overlap may easily be obtained during application. This allows the overlap to be very controllable and predictable. The markings may e.g. comprise markings arranged along at least one line extending in the circumferential/transversal direction of the compression garment.

The markings may be arranged or extend over a substantial part of the compression garment, such as extending over more than 50% of the circumference of the garment. However, alternatively the markings may comprise markings having a limited extension in the width and length direction of the compression garment.

The markings may e.g. comprise characters, digits and/or colour or pattern codes forming a continuous or discontinuous scale in the length direction of the compression garment. This may also enable the use of different markings for different folding, thereby providing a multitude of different pressure profiles.

The markings may also be repeatedly and equidistantly arranged over a part of the lengthwise extension of the compression garment.

The marking(s) may also be arranged to provide a plurality of defined overlaps when folding a part of the sheet over another part of the sheet, thereby forming a corresponding plurality of defined overlaps transversally encircling the full circumference of a part of said body part.

The marking(s) are preferably visually and/or tactilely discernible. For example, the markings may be printed markings, discernible structures in the textile material, openings, etc.

In one line of embodiments, the garment is provided with at least one opening, wherein the overlap is formed by folding a part of said garment from said opening towards the rest of the garment, thereby forming an overlap at least in the vicinity of said opening. For example, the compression garment may be formed as a stocking or a sock, whereby the folding may occur at the upper part.

In another line of embodiments, the garment may have a tubular shape having two openings, wherein the markings may be defining overlaps when folding the sheet from one or both of said openings. This is e.g. advantageous when the compression garment is used as a sleeve, a leg covering or the like.

In yet another line of embodiments, the compression garment may have a tubular shape having two openings and the sheet being arranged in a torus shape, forming a double layer tube, wherein difference in folding makes different parts overlap each other.

In another line of embodiments, the sheet of the garment in one disposition encloses an internal cavity, and in a second disposition is folded so that one part of the sheet is inverted into the remaining part of the sheet, thereby forming a double layer shape having one opening.

The sheet of the compression garment may have a uniform pressure profile. However, it is in many cases advantageous to use a non-uniform pressure profile in the longitudinal direction. The pressure profile may in such embodiments be essentially uniform, but having one or more areas with increased pressure. The pressure profile may also be continuously or discontinuously varying in the length direction. For example, the pressure may be continuously rising or falling from one end to the other, or form a sinusoidal curve, or the like.

The elastic material preferably has an elastic property such that the stretching force and the circumference cancel out in Laplace's law. Hence, such a material will produce the same or essentially the same pressure profile for a variety of dimensions, so that a single size of the compression garment will produce the same pressure profile for a large range of body part sizes. This makes the product very versatile, since the same garment can be used for body parts of different sizes, such as on different parts of the legs and/or arms. It also makes production and distribution easier and more cost-efficient, since one and the same size of the garment can be used by users having different sizes, so that only one or a few different sizes need to be provided to serve a full range of body sizes.

An elastic material having such elastic properties is per se disclosed in the PCT-application PCT/EP2013/065281 by the same applicant, said document hereby being incorporated in its entirety by reference.

More specifically, it is preferred that the elastic property of the elastic material is such that when the same length of unstretched elastic material is stretched to encircle a circular object with different circumferences at different yield rates the pressure exerted by the elastic material varies less than 30% over a range of approximately circular circumferences providing a range of yield rates from $\lambda_1$ to $\lambda_2$, wherein $\lambda_2/\lambda_1 > 1.8$.

The use of such a material is based on the realization that when an elastic bandage is stretched and wrapped around a body part, the body part will be compressed by a normal force. As the force locally is close to constant, it is convenient to instead consider the pressure, the force per surface area. Theoretically, this pressure is given by the stretching force in the compression garment, divided by the product of the stretched elastic garment width and the local radius of curvature. For body parts that can be considered to have circular cross sections, such as limbs, the radius of curvature can be approximated by the radius of a circle with the same circumference as the body part.

By use of such an elastic material, the same garment size may also be used on different individuals, different body parts, etc., since the same result will automatically be achieved regardless of the size of the circumference—and hence the radius of curvature, over a large range of diameters.

The engineering principles of this material will now be explained in the context of an elastic bandage, as in the above-discussed PCT-application PCT/EP2013/065281. The same principles apply when using the material in a compression garment. If we consider a stretched elastic bandage wrapped around the axis of symmetry of the frustum of a right circular cone with radii ranging from $r_1$ to $r_2$, where $r_1 < r_2$, then the pressure on the cone is given by the formula $$p = \frac{Fn}{wr},$$

where F is the longitudinal force in the elastic bandage; n is the number of layers; w is the width of the elastic bandage; and r is the radius. In the medical literature, this formula is sometimes referred to as Laplace's law. This formula assumes that the longitudinal stress in the elastic bandage—which is easy to measure—coincides with the hoop stress. However, if the elastic bandage progresses along the axis of the cone as it is wrapped around the cone, then these quantities no longer coincide. Nevertheless, the difference is quite small when the overlap is 50 percent or more, and it can usually be accounted for by calibration. Furthermore, in this case the number of layers n should be interpreted as the average number of layers, where the boundary effects are ignored. That is, if the elastic bandage at every turn is shifted a fraction t of the bandage width, then n is the linear interpolation, as a function of t, between 1/t rounded down to the nearest integer and 1/t rounded up to the nearest integer. The closer 1/t is to an integer, the closer to constant the average number of layers will be.

Now we may introduce the stretch quotient, also referred to as the yield rate, $\lambda$, defined by $$\lambda = \frac{L}{L_0}$$

where L, $L_0$ are the stretched and unstretched lengths, respectively.

Further, the stretched length will be $L = 2\pi r$, or equivalently $$r = \lambda \frac{L_0}{2\pi},$$

and from this we see that $$p = \frac{2\pi F n}{w \lambda L_0} \quad (1)$$

Now, let $p_0$ denote the desired lowest pressure and, by way of example only, assume that the desired smallest overlap is 50 percent, so that n=2. Then as long as $$\frac{F}{w\lambda} = \frac{p_0 L_0}{4\pi} \quad (2)$$

the applied pressure is $p_0$ when the elastic bandage is wrapped with an overlap of 50 percent. By changing the overlap, and hence n, the applied pressure changes by a factor of n/2.

With the elastic bandage material of the present invention, this relation (2) approximately holds for stretch quotients covering all relevant radii. That is, it approximately holds at least for $\lambda$ satisfying $$\frac{2\pi r_1}{L_0} \le \lambda \le \frac{2\pi r_2}{L_0}. \quad (3)$$

In practice, $$\frac{F}{w\lambda}$$

is measured experimentally and is found to be approximately a constant K for $\lambda$ in some interval $\lambda_1 \le \lambda \le \lambda_2$. In this case, we may choose the unstretched length $L_0$ as $$L_0 = \frac{4\pi K}{p_0},$$

and the pressure $p_0$ then satisfies $$\frac{2\lambda_1 K}{r_1} \le p_0 \le \frac{2\lambda_2 K}{r_2}$$

In particular, one single elastic bandage type may be used for multiple target pressures by varying the length $L_0$. Furthermore, we see from (1) that if the left hand of (2) is constant up to a certain relative error, then the pressure is constant up to the same relative error, when n, w, and $L_0$ are fixed.

As the compression garment of the present invention satisfies equation (2) with only a small error, the present invention offers a compression garment that yields a homogeneous pressure on body parts of varying circumference.

It may also easily be made sure that the compression garment is not used outside the domain given in (3). For example, it is sufficient to measure—or often to just estimate the size of—the body part where it is the narrowest and also where it is the widest. In the case of legs, this is usually at the ankle and at the upper thigh, respectively, and in all cases it suffices to measure the circumference of the body part at two points only.

That the elongation is within the desired domain can also be verified using any of the techniques known in the art for indicating elongation. For instance, one may print two sets of rectangles on the compression garment with side lengths chosen so that they become squares at elongations $\lambda_1$ and $\lambda_2$, respectively. In this latter case, it is not necessary to do any measurements of circumference. Furthermore, these elongation indicators may be incorporated in the markings used to define the folded overlaps.

By way of example, consider using the compression garment on legs. If the person is standing up, then gravity will cause the pressure in the blood vessels to increase in the distal direction. According to physiological studies, the increase of pressure at a point is approximately proportional to the height of the blood column between the point and the heart. In a healthy blood vessel, this increase in pressure is countered by a corresponding increase in pressure in the surrounding tissue, since the densities are almost the same. However, in case of certain medical conditions, such as deep venous insufficiency, an additional pressure has to be applied at all times, and to achieve this, the forces of gravity might need to be countered by applying the bandage with an decreasing pressure in the proximal direction.

As the present invention makes it possible to vary the pressure in the longitudinal direction of the body part, a compression garment may be applied to automatically yield a decreasing pressure in the proximal direction.

In a similar manner, other types of graduated pressure—including arbitrary pressure changes in the longitudinal direction of the body part—can also be achieved, including a pressure that increases rather than decreases in the proximal direction.

For certain medical conditions, it is desired that the applied pressure on the leg is higher when standing up than when lying down. Customarily, this is achieved by making use of the fact that fluid accumulates in the legs, thereby increasing their volume, when standing up. If the compression garment is such that the force increases rapidly with the elongation, then the increase in volume causes an increase in pressure.

With a compression garment of the present invention, which preferably satisfies equation (2), then there will be no increase at all in the pressure from the compression garment when the person stands up. For some situations, such as for certain patients who are mainly lying down, this is desirable. If, however, an increase in pressure is desired, this can still be achieved using the present invention: e.g. by applying a specified folding.

Preferably, the elastic properties of the elastic material are such that the pressure exerted by such turns having the same length of unstretched material varies less than 20% over a range of circumferences providing a range of yield rates from $\lambda_1$ to $\lambda_2$, and even more preferably varies less than 10%. Further, it is preferred that the range of yield rates in which this property exist are such that $\lambda_2/\lambda_1 > 2.5$, and most preferably $\lambda_2/\lambda_1 > 3.0$. Hereby, an even more flexible and useful compression garment is obtained.

In particular it is preferred that the elastic properties of the elastic material are such that the pressure exerted by the material varies less than 20% over a range of circumferences providing a range of yield rates from $\lambda_1$ to $\lambda_2$, wherein the range of yield rates in which this property exist are such that $\lambda_2/\lambda_1 > 2.5$, Even more preferred, the elastic properties of the material are such that the pressure varies less than 10% over a range of circumferences providing a range of yield rates from $\lambda_1$ to $\lambda_2$, wherein the range of yield rates in which this property exist are such that $\lambda_2/\lambda_1 > 3.0$, Hereby, an even more flexible and useful compression garments are obtained.

The elastic material is preferably a textile, and preferably comprising both elastic and non-elastic yarns and threads.

The elastic material may comprise synthetic fibres selected from the group consisting of polyester, polyamide, polypropylene or PLA (polylactic acid). The elastic material may further comprise natural fibres, such as cotton or regenerated fibres such as viscose or a mixed spun yarn with multifilament synthetic fibres and natural staple fibres or other mixtures thereof.

In a preferred embodiment, the elastic material comprises threads or yarns of at least one of: elastomeric polymers such as natural rubber, polyisoprene, synthetic rubber, a mix of polyisoprene rubber and styrene butadiene copolymer or a mix of thermoplastic and elastomeric polymers such as polyurethane-polyurea copolymer, and other mixtures thereof.

The elastic material is preferably a woven or knitted material.

It has been found that these elastic materials are very useable for obtaining the above-discussed elastic properties.

The above-discussed compression garment is particularly useful for applying a controlled compression to parts of the body, for use in at least one of prophylactic treatment, therapeutic treatment, performance-enhancing and recovery. However, in addition to compression therapy, it is also useful for other known uses of compression garments.

The adjustable compression garment of the present invention is useable to create localized pressure, e.g. to inhibit or treat established swelling. The compression garment may also be used to enhance the venous return in individuals with either venous insufficiency or obstruction. The compression garment is also useable for non-medical indications, to reduce the risk of muscle sprain and strains and to improve recovery after physical activities.

A particular line of medical use for the compression garments is for compression therapy of venous insufficiency, oedema and venous ulcers. Another line of medical use is localized compression treatment of subcutaneous, or muscle, bleeding following for example surgery or blunt trauma. Yet another use is to facilitate the transportation of blood in the deep system. A subgroup of compression garments with this purpose deliver graduated compression.

The compression garment is also useable to prevent swelling to emerge or reduce risk for venous thrombus formation. Examples of the latter are in connection to surgery or intercontinental flights. Swelling can also commonly be seen in connection to heart failure.

The compression garment is also useful as sport equipment, in order to: improve recovery, faster warm up and enhance overall circulation, enhance stability and agility, reduce fatigue and reduce damage.

Further, even though the compression garment is intended for use on humans, it is equally possible to use the compression garment on animals.

According to another aspect of the invention there is provided an integrated compression garment assembly, comprising at least two integrated sections, wherein each section comprises a compression garment of the type discussed in the foregoing. The integrated sections may e.g. be connected by seams, adhesive or other connection means. However, the integrated sections may also be connected by being made of a common sheet of material, so that the material sheet forming one section extends into, and forms, also the other section(s). The sections may be arranged to encircle different body parts. For example, one section may be arranged to be applied on the leg, another section on the foot, yet other sections on each separate toe, etc. Similarly, separate sections may be arranged to be applied on each or some of the fingers, in case of a garment to be used over the hand and/or arm.

According to another aspect of the invention there is provided a method of adjusting the range of compression level applied by a compression garment, comprising:

providing a unitary single sheet of elastic material arranged to encircle the full circumference of a body part;

folding the sheet in at least one predefined way, the folding forming one or more defined overlap(s) forming at least two overlaying layers of the sheet encircling the full circumference of a part of said body part.

Hereby, similar advantages and specific features as discussed above in relation to the first aspect are obtainable and useable.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIGS. 10-12 show a cross-sectional view of another embodiment of a compression garment for a body limb in accordance with the present invention. The figures illustrate various intermediate steps during application of the garment.

FIGS. 13-16 show perspective view of another embodiment of a compression garment, here for use on a head, in accordance with the present invention. The figures illustrate various intermediate steps during application of the garment.

FIG. 17 shows the garment in a non-applied state, and FIG. 18 shows the garment in an applied state.

DETAILED DESCRIPTION OF PREFERRED EMBODIMENTS

Figure 1:
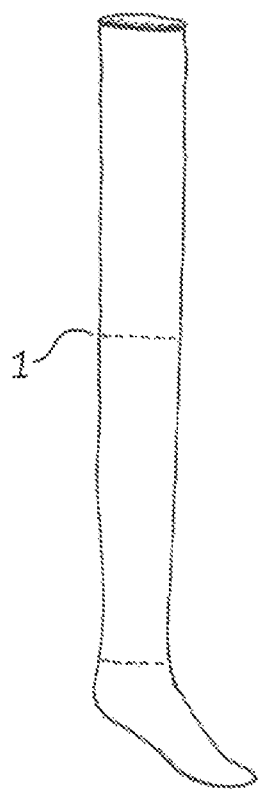
FIGS. 1-4 show perspective views of an embodiment of a compression garment for a body limb in accordance with the present invention.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention. Further, the same reference signs are used to designate equal or similar parts throughout the drawings.

Figure 2:
Figure 3:
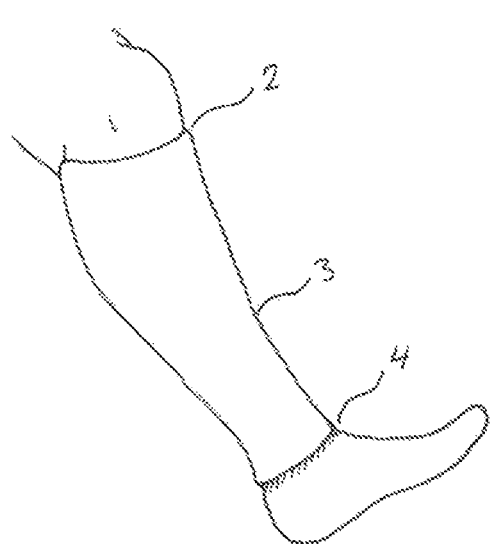
Figure 4:
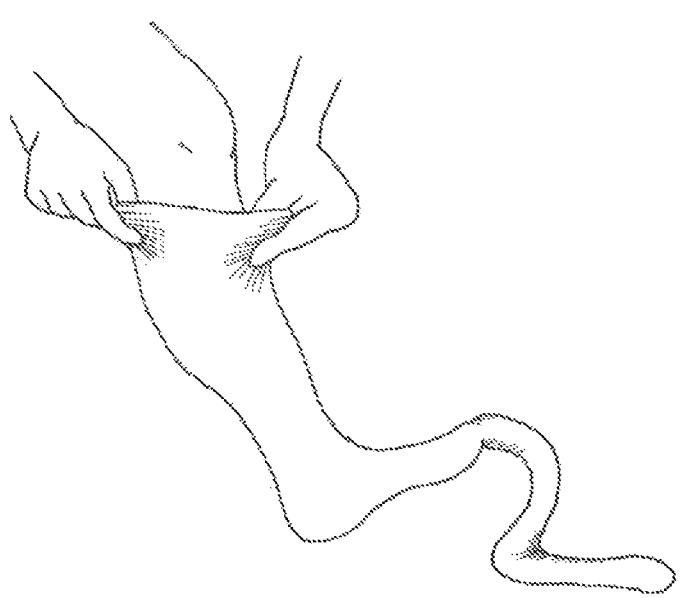

In FIG. 1, a long compression garment, here in the form of a sock, is illustrated with an optional marking for an optional folding position 1. By folding, the upper part of the sock over the remainder of the sock, a different pressure profile may be obtained. In FIGS. 2 and 3, two preferred configurations of the sock in FIG. 1 are illustrated. In FIG. 2 the sock is applied as a single layer in its full length. In FIG. 3, the upper part is folded on top of itself, which creates a double layer, and increased pressure. The double layer starts at the fold 2 and ends at a point that might be marked 4. In FIG. 4, there is an illustration on how the sock is applied.

Figure 5:
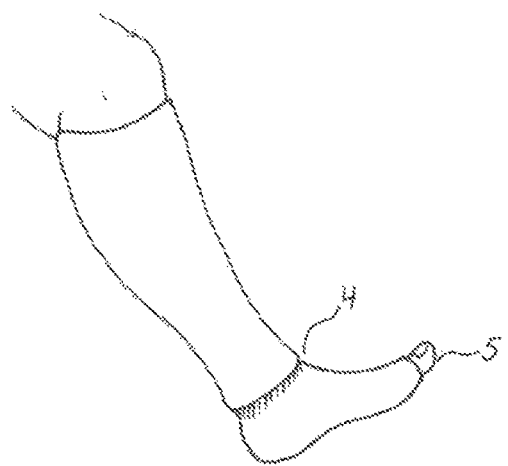
FIGS. 5-9 show perspective views of other embodiments of a compression garments for body limbs in accordance with the present invention.

FIG. 5 is an embodiment of the garment similar to the one in FIG. 1, but here the sock is open for the toes 5, i.e. the garment is topologically a cylinder.

Figure 6:
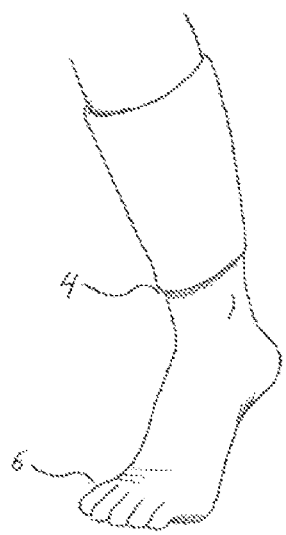

In FIG. 6, there is another embodiment similar to the one of FIG. 1, but this version of the compression garment includes compression on separate toes 6.

Figure 7:
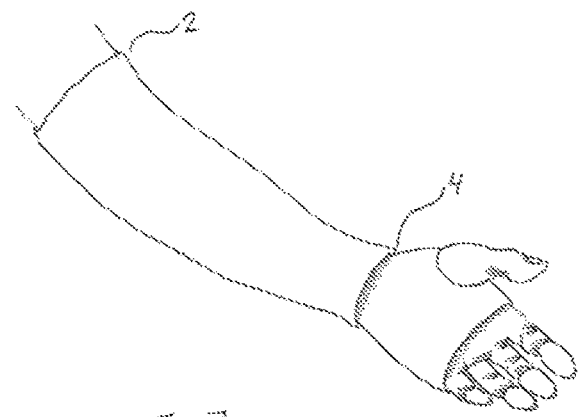

FIG. 7 illustrate a tubular compression garment similar to the one in FIG. 1, but the compression garment in this embodiment is instead arranged to be applied as a sleeve on an arm. Such a sleeve may extend only from the wrist and upwards. However, preferably, as is also illustrated in FIG. 7, the sleeve may extend over the wrist and over the upper part of the hand. In such a realization, the sleeve is also preferably provided with a lateral opening for the thumb.

Figure 8:
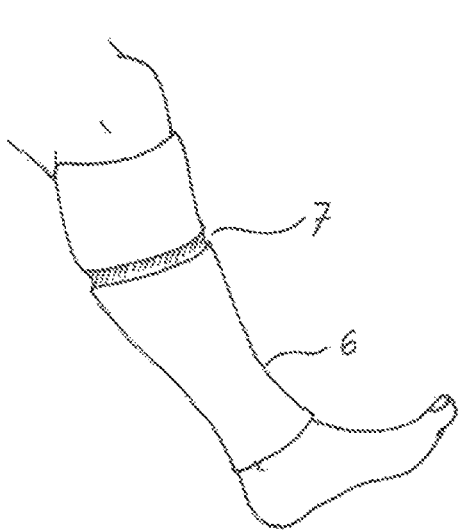
Figure 9:
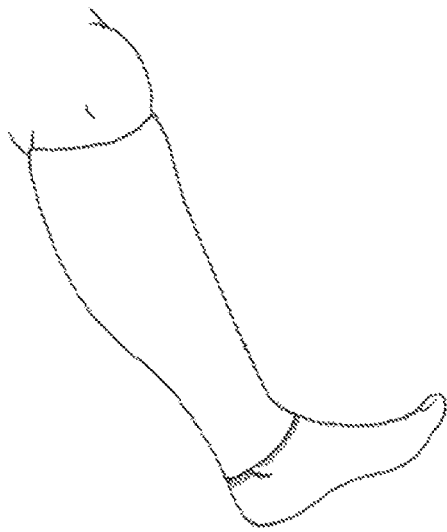

FIG. 8 shows a cylindrical compression garment that is folded from the upper part, but also folded from below, 6. Such folding may extend over different length, and may e.g. extend so far that the ends meet each other at a certain point 7. Those configurations in which the two ends met can also be realized as a double layered tube, that is as a compression garment which is topologically a torus. A double layer tubular compression garment, a torus, corresponding to that in FIG. 8, is illustrated in FIG. 9. In such embodiments, the pressure profile of the sheet material is preferably non-uniform, as is discussed in more detail in the following. Thus, the overall pressure profile of the compression garment may then e.g. be adjusted by displacing the two layers in relations to each other—which for the case for the cylinder in FIG. 8 means adjusting the meeting point 7 upwards or downwards—something that will be displayed and elaborated with reference to FIGS. 19 to 48.

FIGS. 10-12 illustrate a compression garment in which the sheet in one disposition encloses an internal cavity, as shown in FIG. 10, and in a second disposition, as shown in FIG. 12, is folded so that one part of the sheet is inverted into the remaining part of the sheet. Hereby, a double layer shape is formed, having one opening. The garment of this embodiment is topologically a sphere. FIG. 10 shows the unfolded garment, FIG. 11 how it is folded, during an intermediate step, and FIG. 12 the final, applied state. In this exemplary embodiment, the compression garment is a sock to be applied on a leg, but similar compression garment may also be used for other limbs or the head.

FIGS. 13-16 show how a tubular compression garment can be transformed into a garment which is topologically a multilayered disc, which can be folded and applied to for instance a head. FIG. 13 shows the garment in its tubular form with an upper part 8 and a lower part 9. FIG. 14 illustrates the same garment after twisting the parts 8 and 9 relative to each other. FIG. 15 illustrate the garment in the form of the resulting cap after downfolding the upper part 8. FIG. 16 shows the tubular compression garment applied on a head. By applying the twisting and folding differently on the tube, various configurations having different pressure profiles become possible. Further, if the tubular garment is a torus, it can, as in FIG. 9, get different configurations by sliding the torus in 13 before it is twisted in 14.

Figure 17:
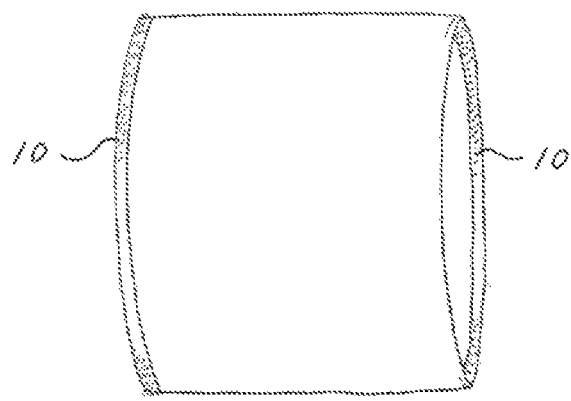
FIGS. 17 and 18 are perspective views illustrating a compression garment in accordance with yet another embodiment of the present invention, where
Figure 18:
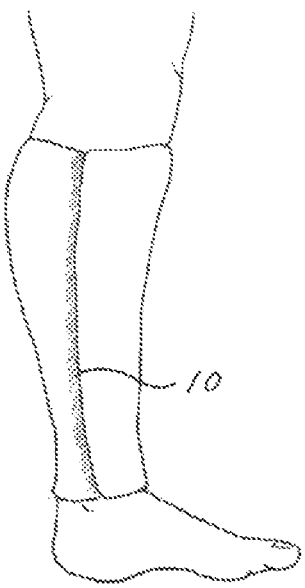

FIGS. 17 and 18 illustrate a compression garment in the form of an openable torus, i.e. having a longitudinal openable seam or connection. FIG. 17 illustrate the garment in its open form, whereas FIG. 18 illustrates the garment when applied on a leg. The sides 10 can be attached to each other using for example hooks and loops. Such an embodiment can for example be useful if one wants to apply the compression garment without threading it over the foot. That might be especially useful for treating animals, such as for example a leg of a horse.

Figure 19:
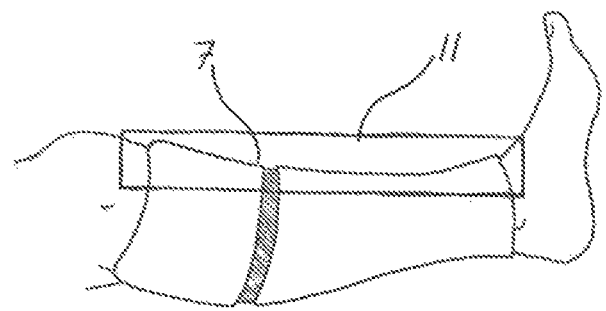
FIG. 19 shows, in a perspective view, an exemplary compression garment in accordance with an embodiment of the present invention, the garment being similar to the one illustrated in FIG. 8.
Figure 20:
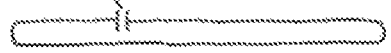
FIG. 20 shows a schematic representation of the folding configuration of the compression garment in FIG. 19, schematically showing the extension of the sheet in the marked area of FIG. 19.

FIGS. 19 and 20 schematically illustrate a specific configuration of the compression garment. This embodiment is similar to the one discussed above with reference to FIG. 8. FIG. 20 illustrate a schematic cross-sectional view of the sheet at the part within the box 11 of FIG. 19. In FIG. 20, the point 12 represents the meeting point 7 of the both folded ends.

The following FIGS. 21 to 45 use the schematic illustration in FIG. 20 to show how one can vary the resulting pressure profiles using different folding configurations based on a few underlying pressure profiles of the unfolded compression garment. Note that an end that has not been folded need not represent an actual end of a garment section, and the same schematic illustration; for instance, the schematic illustration in FIG. 22 can be used to illustrate garment sections of the garments in FIGS. 3, 5 and 9.

Figure 21:
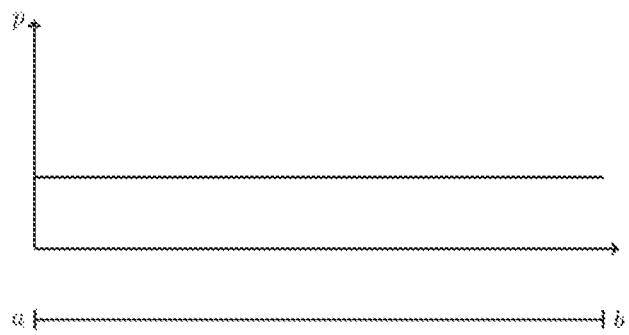
FIG. 21 is a schematic diagram showing a first example of pressure profile in the sheet material of a compression garment in accordance with the present invention.
Figure 22:
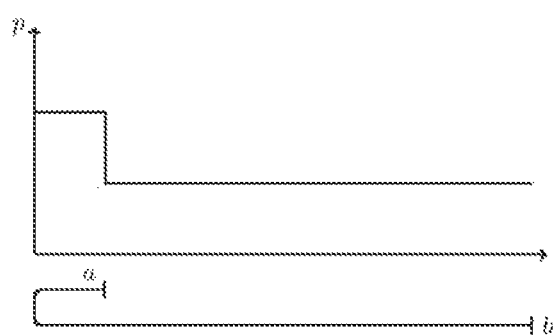
FIGS. 22-24 are schematic diagrams illustrating pressure profiles of the compression garment, when the garment of FIG. 21 is folded in the folding configurations represented schematically beneath each diagram.
Figure 23:
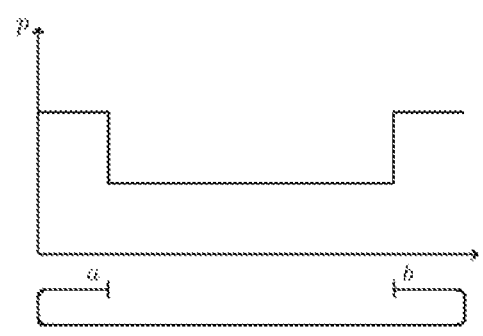
Figure 24:
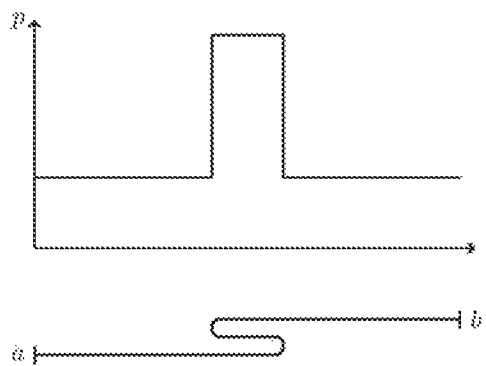

FIG. 21 shows an unfolded garment, and made by a sheet having a uniform pressure profile. By folding at one end of the garment section, as shown in FIG. 22, a localized increase in pressure is achieved in the overlap area, i.e. in the vicinity of the opening where the folding occurred. Folding at both ends, as illustrated in FIG. 23, yields a garment having a lower pressure in the interior section than at the ends. Naturally, the longitudinal extension of all these sections having different pressure can be adjusted. It is also possible to fold the garment at the interior of a section, as shown in FIG. 24, with a z-shaped double fold, which yields a localized area with high pressure.

Figure 25:
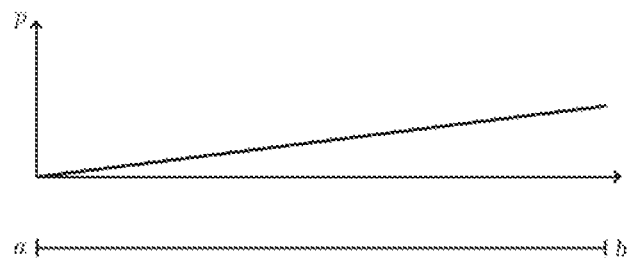
FIG. 25 is a schematic diagram showing a second example of pressure profile in the sheet material of a compression garment in accordance with the present invention.
Figure 26:
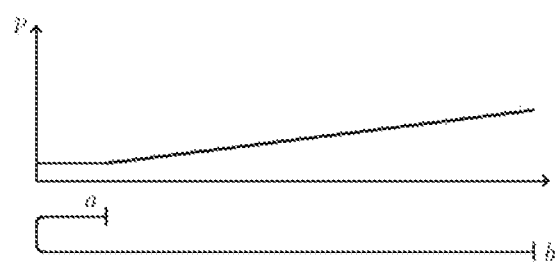
FIGS. 26-30 are schematic diagrams illustrating pressure profiles of the compression garment, when the garment of FIG. 25 is folded in the folding configurations represented schematically beneath each diagram.
Figure 27:
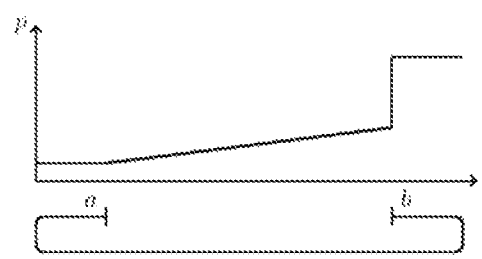
Figure 28:
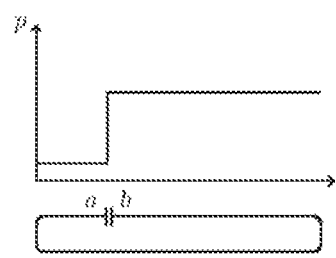
Figure 29:
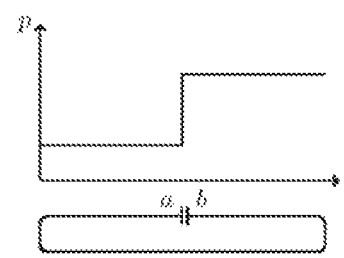
Figure 30:
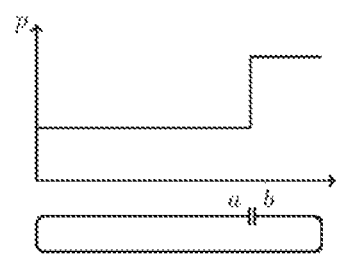

FIG. 25 shows an unfolded garment, and made by a sheet having a linear pressure profile. This garment, when unfolded, consequently exerts a very low pressure at one end, a relatively high pressure at the other end, and a linear transition there between. In this case, folding one of the ends, as illustrated in FIG. 26, or both ends, as illustrated in FIG. 27, yields a constant pressure in the overlap areas. If the folds are extended to meet in the interior of the garment, as shown in FIGS. 28, 29, 30, the pressure increases stepwise at the meeting point and is constant elsewhere. The position of the meeting point determines both the size of the stepwise increase, and where this transition occurs in the longitudinal direction.

Figure 31:
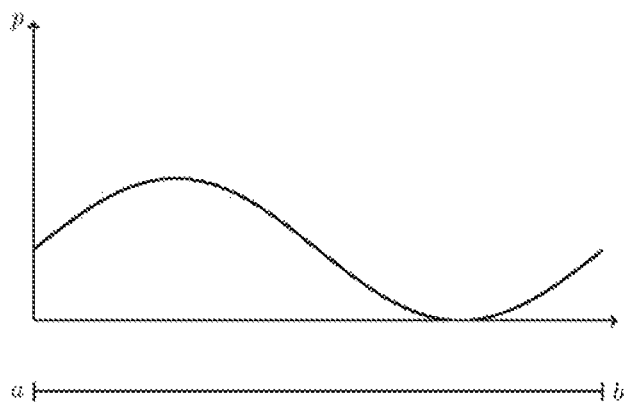
FIG. 31 is a schematic diagram showing a third example of pressure profile in the sheet material of a compression garment in accordance with the present invention.
Figure 32:
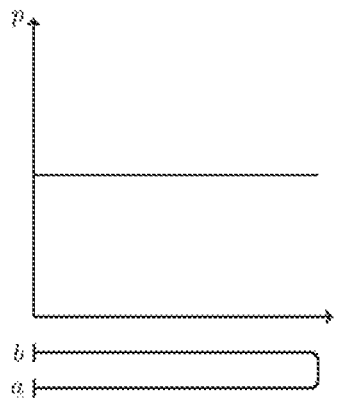
FIGS. 32-34 are schematic diagrams illustrating pressure profiles of the compression garment, when the garment of FIG. 31 is folded in the folding configurations represented schematically beneath each diagram.
Figure 33:
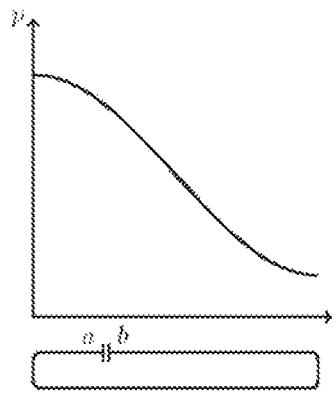
Figure 34:
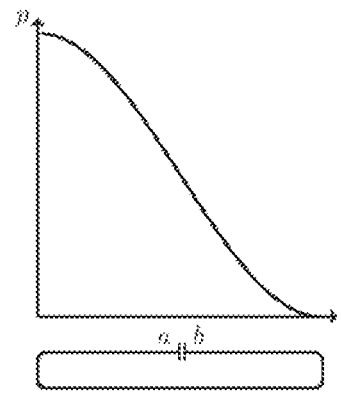

FIG. 31 shows an unfolded garment, and made by a sheet having a pressure profile exhibiting a sinusoidal shape. In this example, the pressure is about the same at the ends and in the centre, whereas the sections there between form a maximum and a minimum, respectively, and continuous transitions there between. If one end of the garment section is folded to meet the other end, a constant pressure profile is achieved, as shown in FIG. 32, and by keeping both ends together and gradually moving their point of contact, various smooth and monotone pressure profiles are achieved, as shown in FIGS. 33, 34.

Figure 35:
FIG. 35 is a schematic diagram showing a fourth example of pressure profile in the sheet material of a compression garment in accordance with the present invention.
Figure 36:
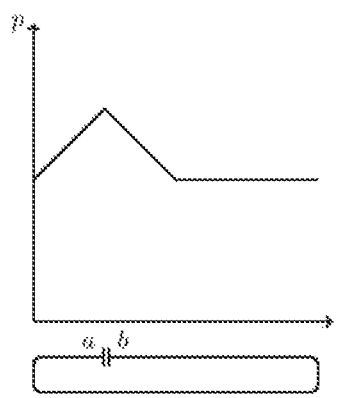
FIGS. 36-41 are schematic diagrams illustrating pressure profiles of the compression garment, when the garment of FIG. 35 is folded in the folding configurations represented schematically beneath each diagram.
Figure 37:
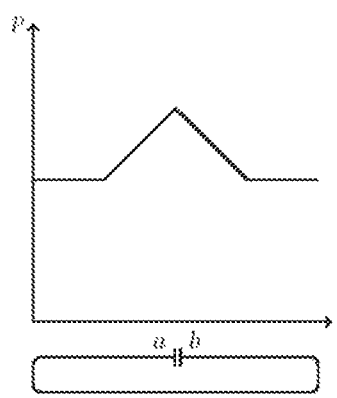
Figure 38:
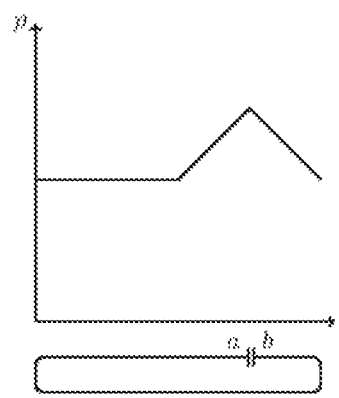
Figure 39:
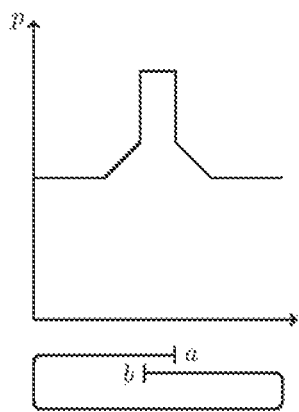
Figure 40:
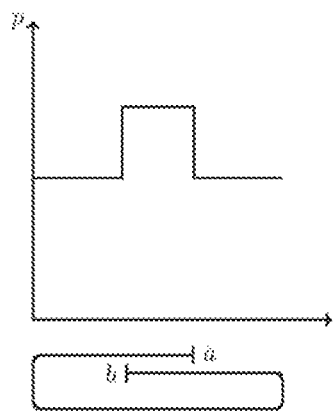
Figure 41:
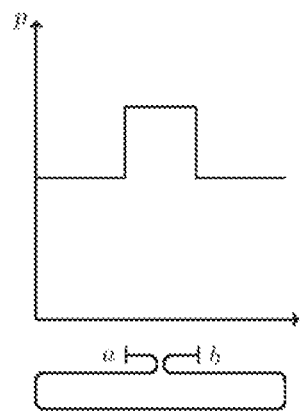

FIG. 35 shows an unfolded garment, and made by a sheet having a pressure profile that linearly increases at the ends of the garment or garment section. If the ends of such a garment are folded to meet in the interior, a continuous increase in pressure is achieved in the interior of the garment section, as shown in FIGS. 36, 37, 38. The folding, and in this case the meeting point for the ends, define where the pressure is increased. By allowing the ends to overlap, an even higher increase in pressure can be achieved, as shown in FIG. 39. Extending the overlap even more, as shown in FIG. 40, yields a stepwise increase in pressure in the interior of the garment section, complementary to that in FIG. 23. The same pressure profile can also be achieved by folding the ends over themselves, as shown in FIG. 41.

Figure 42:
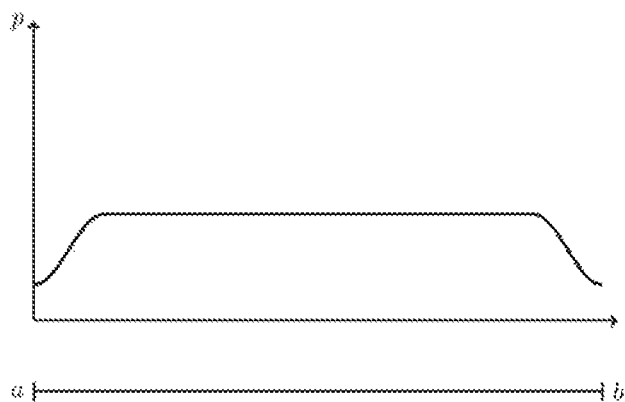
FIG. 42 is a schematic diagram showing a fifth example of pressure profile in the sheet material of a compression garment in accordance with the present invention.
Figure 43:
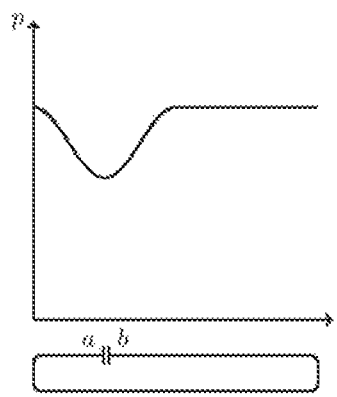
FIGS. 43-45 are schematic diagrams illustrating pressure profiles of the compression garment, when the garment of FIG. 42 is folded in the folding configurations represented schematically beneath each diagram.
Figure 44:
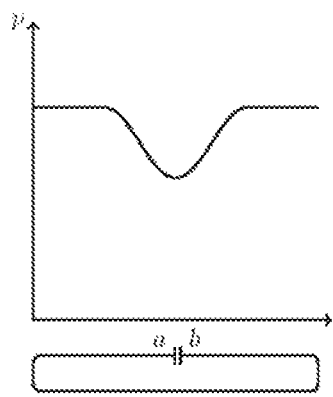
Figure 45:
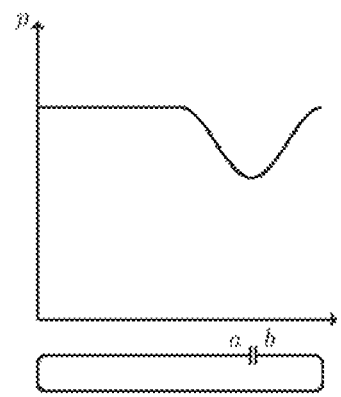

FIG. 42 shows an unfolded garment, and made by a sheet having a pressure profile that smoothly decreases at the ends of the garment section. Folding the ends of the garment so that they meet result in a localized decrease in pressure in the interior of the garment, as shown in FIGS. 43, 44 and 45.

The above-discussed non-uniform pressure profiles of the sheet, and the pressure profiles obtained by various folding configurations are only exemplary, and many other pressure profiles and folding configurations are feasible.

Figure 46:
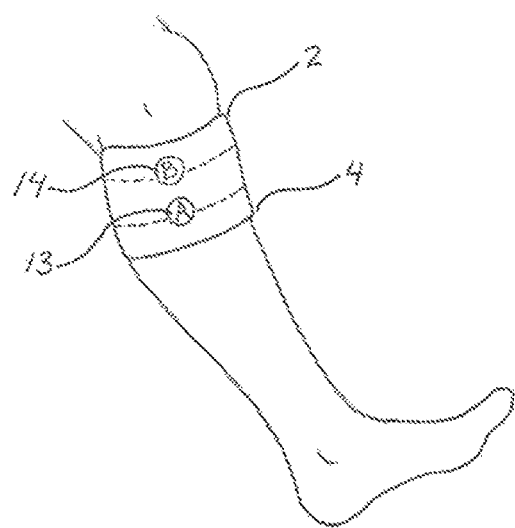
FIGS. 46-50 are perspective views schematically illustrating various embodiments of compression garments in accordance with the present invention, where the garments are provided with markings to indicate predefined folding positions.
Figure 47:
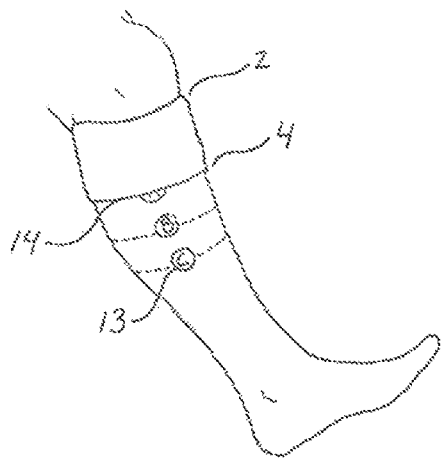

FIGS. 46 and 47 show a pressure indicator/marking for an embodiment of the present invention that has at least one fold at an end of a garment section. Folding the garment at an end of a garment section turns the garment inside out between the fold 2 and the end of the garment section 4, exposing a portion of the interior of the unfolded garment section. In FIG. 46, the interior of the unfolded garment section has one or more markings 13, and the exposed marking 14 that is closest to the fold, 2, indicates the pressure profile. The indicator in FIG. 47 is similar, but has instead markings 13 on the exterior of the unfolded garment section, utilizing the fact that this side of the garment section is hidden, either covered or turned inside out, from the end of the garment section 4 to the line of contact between 4 and the garment section.

An indicator can be supplied for each fold if the garment section is folded at multiple ends, and different ends need not use the same sort of indicator. The same sort of indicator can also be used if the garment section is folded multiple times at a single end.

Figure 48:
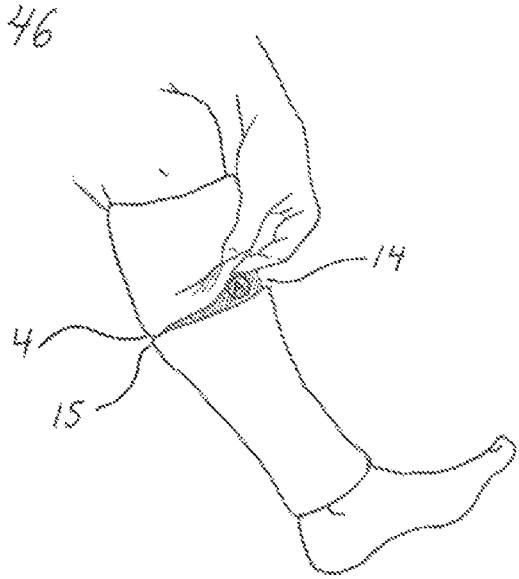
Figure 49:
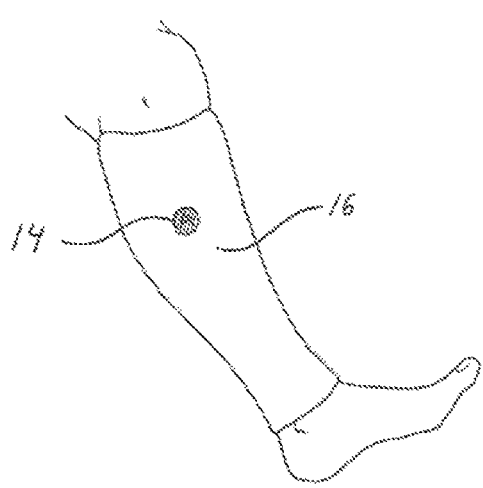
Figure 50:
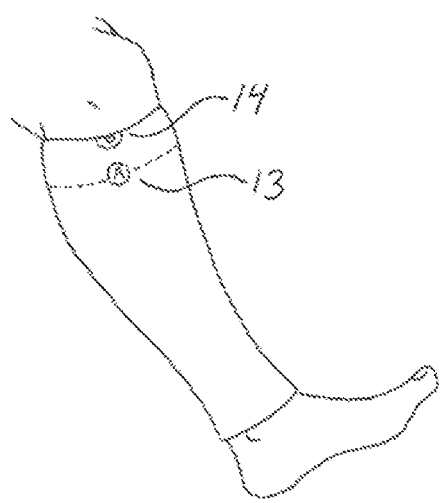

FIGS. 48-50 show how the indicator/marking can be simplified in the case when the garment section is folded in such a way that two ends meet, including the case where the two ends are fused together and the garment section is topologically equivalent to a torus. In FIG. 48, the ends 4 and 15 of the garment section meet along different transversal sections of the garment section. Manually slightly lifting an end 4 or 15 of the garment section exposes a single marking 14 of the markings on the exterior of the unfolded garment section. Similarly, the garment in FIG. 49 has a portion 16, such as a hole or an at least semitransparent fabric, which exposes a marking 14 on the interior layer of the garment section. In FIG. 50, transversal markings 13—which are initially facing the skin—become exposed as the folding is adjusted, so that the pressure profile can be indicated on the marking 14 closest to a specified end of the garment section.

Figure 51:
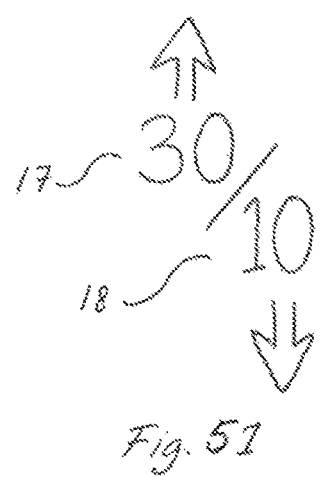
FIGS. 51-57 are schematic views of other possible markings useable in compression garments in accordance with the present invention.

FIGS. 51 to 55 show different embodiments of a single pressure profile indicator 14. The indicator in FIG. 51 shows the pressures 17 and 18, here 30/10, or in a different embodiment the mean pressures, in a customary unit such as mmHg for two subsections of the garment section, where the subsections may either be fixed—such as the upper and lower half of the garment section—or depend on the position of the indicator.

Figure 52:
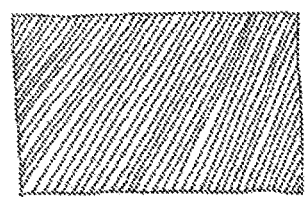
Figure 53:
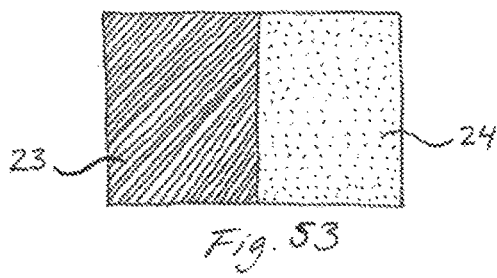

FIGS. 52 and 53 illustrate that the indicator can be based on different color or various tactile structures, one can also use different overlay effects from the different layers—that can be semitransparent—such as moiré effects.

Figure 54:
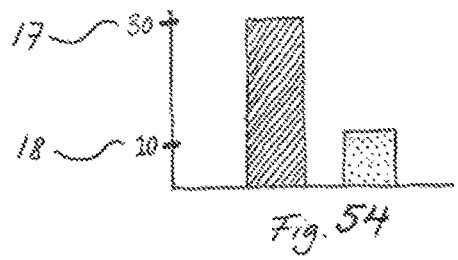
Figure 55:
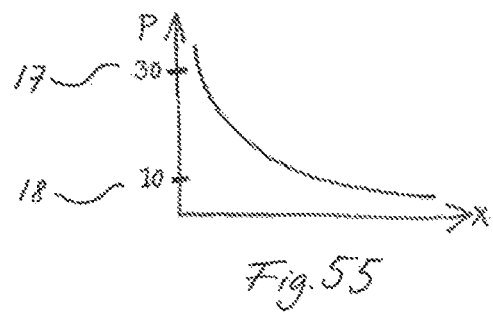

FIGS. 54 and 55 illustrate two extensions of the indicator/markings in FIG. 51, showing the exact pressure profile in the form of different charts. In addition to the graphical representation, numeric values indicating for instance the maximum 17 and minimum 18 or the mean pressure can be shown in the charts.

Figure 56:
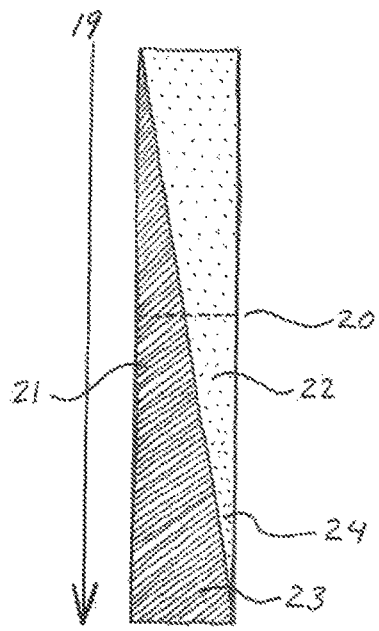
Figure 57:
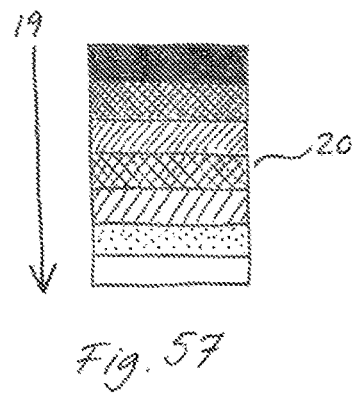

FIGS. 56 and 57 show a continuum of indicators/markings, where 19 is the longitudinal direction of the garment. Each transversal section 20 determines a certain pressure profile, and e.g. the markings shown in FIGS. 46-50 can be used to identify such a section. In FIG. 56, each transversal section 20 determines two lengths 21 and 22—similar to FIG. 54—having a constant sum, making it suitable to illustrate pressure profiles such as those in FIGS. 28-30. In one embodiment, the two areas 23 and 24 have different colors, in another they can be tactilely discerned, and in a third only one of the sections may be present at each transversal section. In FIG. 57, there is instead a plurality of transversal sections 20, which in one embodiment has different colors, in a second embodiment has different patterns or in a third embodiment can be tactilely discerned.

Figure 58:
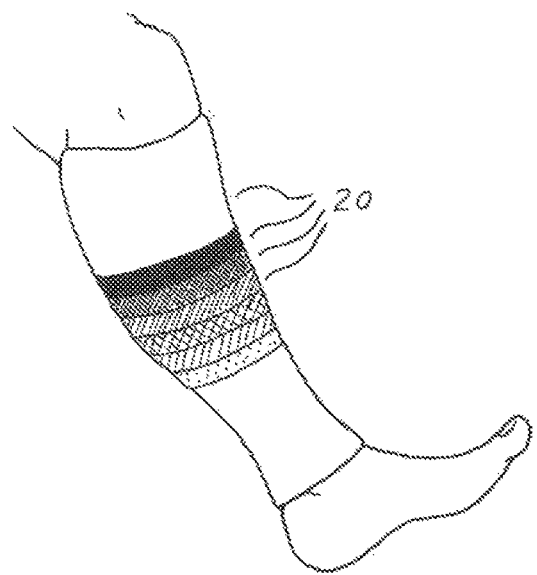
FIGS. 58-60 are perspective views schematically illustrating other embodiments of compression garments in accordance with the present invention, where the garments are provide with markings to indicate predefined folding positions.
Figure 59:
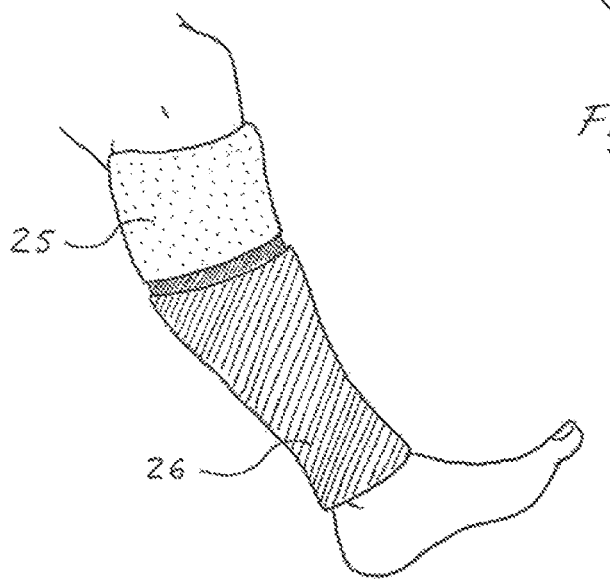
Figure 60:
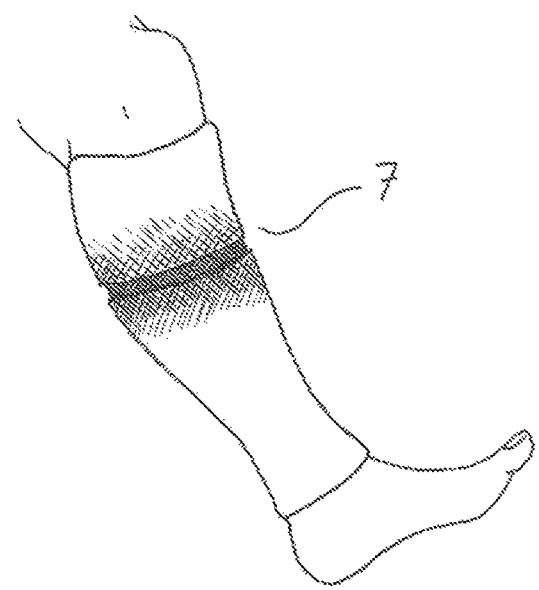

FIG. 58 shows a garment with transversal sections 20 which can be discerned on the outermost layer of the garment, where each transversal section indicates the pressure or relative pressure exerted on the body part at that transversal section. In the embodiment in FIG. 59, suitable for instance for the pressure profiles in FIGS. 28-30, the parts 25 and 26 of the garment can have different colors to indicate that the pressure exerted by 25 is lower than that exerted by 26. In another embodiment illustrated in FIG. 60, suitable for instance for the pressure profiles in FIG. 36-38 or 43-45, the transversal sections 20 indicates which sections of the garment that exerts a different pressure from the rest. In yet another embodiment—suitable for garments with a free end, such as the garment in FIG. 8—the ends of the garments function as the transversal sections 20.

Furthermore, all the preceding indicators may be used together. For instance, each transversal section 20 in FIG. 57 can also have numerical indicators 17 and 18 like those in FIG. 51, an indicator like that in FIG. 56 can be used to show how much further the pressure profile may be adjusted, and additionally an indicator like that in FIG. 59 to show which part of the garment that exerts the highest pressure.

However, many other types of markings and indicia are also feasible for conferring information to the user of how to fold the compression garment to obtain a desired pressure profile.

There are various ways to manufacture the pressure garments as discussed in the foregoing.

One preferred embodiment is weft knitting. In this technique elastic threads are incorporated into the textile construction in order to give the textile material its characteristic stretch properties for pressure garments. The elastic threads are preferably inlayed into the knitted structure under a certain elongation (tension). The elastic threads are also preferably incorporated as a continuous inlay, into the knitted loops; hence the elastic thread never creates any loops. Another way to incorporate the elastic threads is by using tuck knitting, where the elastic yarn can be knitted as a tuck every 2nd, 3rd, 4th . . . stitch.

The ground yarn in the construction can consist of only inelastic yarns, only elastic yarns, but preferably a combination of inelastic and elastic yarns. There are numerous ways to knit a stretch fabric. In one preferred embodiment the ground construction is a rib knit, e.g. 1:1 rib, 1:2 rib, 2:2 rib or the like. In another embodiment the ground construction could be shifted in different parts of the garment, in order to e.g. create a stiffer or more elastic local area on a certain part of the garment.

There are at least two possible weft knitting methods for this purpose. In one embodiment one could use circular weft knitting. This enables a good way to manufacture a tube with open ends. There are however circular knitting machines where e.g. toes and heels are possible to knit. Another embodiment is flat weft knitting. This technique enables a wider spectrum of different shapes. Both in a garment shaped like a single tube as well as in a so-called "whole garment" with a more complex shape e.g. in a garment with integrated toes or fingers.

Yet another technique to manufacture the described pressure garment is warp knitting. The construction should preferably include both inelastic yarns and elastic threads to get the preferred elastic properties. In one embodiment a tube can be produced on a Raschel warp knitting machine, with two needle bars, where the ground construction is knitted on the needles of both beds and the elastic yarn is inlayed transverse to the knitted whales in order to bind the construction together but also to give the textile its elastic properties.

In yet another embodiment, flat warp knitting is used on a Raschel warp knitting with one needle bed. Here, the maximum length of e.g. a tube would have the same length as the needle bed. In this technique a flat fabric is produced, that can be folded lengthwise and sewn together in order to form e.g. a tube or a sock. Another technique to manufacture a flat textile that can be sewn together is to use the above described flat weft knitting.

In one embodiment an over-lock seam is used to sew the flat textile surfaces together. Another seam can for example be a flatlock seam, avoiding seam allowance that can cause marks on the skin. In another embodiment welding is used to merge the two textile surfaces together, in order to form a tube or a sock. One can use solely thermoplastic material in the textile but preferably a thermoplastic tape is used, that works as an adhesive between the two surfaces.

The invention has now been disclosed by reference to preferred embodiments. However, it is to be acknowledged by the skilled addressee that several further modifications are feasible. For example, other elastic materials, and combinations of in-elastic and elastic materials may be used, other production technologies may be employed, etc. Further, the markings defining the folding may be realized in many different ways, some of which have been disclosed in the foregoing. However, many other alternative embodiments would be feasible to the same or similar ends.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A compression garment providing an adjustable pressure towards a body part, comprising a unitary single sheet of elastic material arranged to encircle the full circumference of a body part, the sheet being folded or arranged to be folded in at least one predefined way, wherein the sheet when folded is configured to form one or more defined overlap(s) forming at least two overlaying layers of the sheet encircling the full circumference of a part of said body part, wherein the sheet comprises a plurality of markings indicating a plurality of defined overlaps for a part of the sheet folded over another part of the sheet and providing a corresponding plurality of compression profiles.

2. The compression garment of claim 1, wherein the garment is provided with at least one opening, said overlap being formed by folding a part of said garment from said opening towards the rest of said garment, thereby forming an overlap at least in the vicinity of said opening.

3. The compression garment of claim 1, wherein the garment has a tubular shape having two openings, wherein said plurality of markings are defining overlaps when folding the sheet from one or both of said openings.

4. The compression garment of claim 1, wherein the plurality of markings provide a plurality of defined overlaps when folding a part of the sheet over another part of the sheet, thereby forming a corresponding plurality of defined overlaps concentrically encircling the full circumference of a part of said body part.

5. The compression garment of claim 1, wherein the elastic material comprises synthetic fibres selected from the group consisting of polyester, polyamide, polypropylene or PLA (polylactic acid).

6. The compression garment of claim 1 wherein the elastic material further comprises natural fibres.

7. The compression garment of claim 1, wherein the elastic material comprises threads or yarns of at least one of: elastomeric polymers.

8. The compression garment of claim 1, wherein the elastic material is a woven or knitted material.

9. The compression garment of claim 1, wherein the body part is at least one of a body limb and a body head.

10. The compression garment of claim 1, wherein the plurality of markings are visually and/or tactilely discernible.

11. The compression garment of claim 1, wherein the garment has a tubular shape having two openings and the sheet being arranged in a torus shape, forming a double layer tube, wherein difference in folding makes different parts overlap each other.

12. The compression garment of claim 1, wherein the sheet of the garment in one disposition encloses an internal cavity, and in a second disposition is folded so that one part of the sheet is inverted into the remaining part of the sheet, thereby forming a double layer shape having one opening.

13. The compression garment of claim 1, wherein the sheet has a non-uniform pressure profile in its longitudinal direction.

14. The compression garment of claim 1, wherein the plurality of markings form a continuous or discontinuous scale in a length direction of the compression garment.

15. The compression garment of claim 14, wherein the plurality of markings comprise at least one of characters, digits, color and pattern codes.

16. The compression garment of claim 1, wherein the plurality of markings are repeatedly and equidistantly arranged over a part of a lengthwise extension of the compression garment.

17. The compression garment of claim 1, wherein the unitary single sheet of the compression garment has a non-uniform pressure profile in a length direction.

18. The compression garment of claim 17, wherein the non-uniform pressure profile has an essentially uniform part and one or more parts with increased pressure.

19. The compression garment of claim 17, wherein the pressure of the pressure profile varies continuously or discontinuously in the length direction.

20. The compression garment of claim 17, wherein the pressure of the pressure profile varies linearly in the length direction.

21. The compression garment of claim 17, wherein the pressure of the pressure profile varies as a sinusoidal curve.

22. An integrated compression garment assembly, comprising at least two integrated sections, each section comprising a compression garment in accordance with claim 1.

23. A method of adjusting the range of compression level applied by a compression garment, comprising:
providing a unitary single sheet of elastic material arranged to encircle the full circumference of a body part, wherein the sheet comprises a plurality of markings indicating a plurality of defined overlaps for a part of the sheet folded over another part of the sheet and providing a corresponding plurality of compression profiles;
folding the sheet in at least one predefined way, wherein the sheet when folded is configured to form one or more defined overlap(s) forming at least two overlaying layers of the sheet encircling the full circumference of a part of said body part.

24. The method of claim 23, wherein the plurality of markings form a continuous or discontinuous scale in a length direction of the compression garment.

25. The method of claim 23, wherein the plurality of markings are repeatedly and equidistantly arranged over a part of a lengthwise extension of the compression garment.

* * * * *